United States Patent [19]

Ahmed et al.

[11] Patent Number: 5,281,673
[45] Date of Patent: Jan. 25, 1994

[54] SUPERABSORBENT POLYMERS

[75] Inventors: Iqbal Ahmed, Bartlesville, Okla.; Henry L. Hsieh, Pittsboro, N.C.

[73] Assignee: Phillips Petroleum Company, Bartlesville, Okla.

[21] Appl. No.: 11,917

[22] Filed: Feb. 1, 1993

Related U.S. Application Data

[62] Division of Ser. No. 873,259, Apr. 24, 1992, Pat. No. 5,225,506.

[51] Int. Cl.$^5$ .................. C08F 251/00; C08F 255/00
[52] U.S. Cl. .................... 525/281; 525/291; 525/293; 525/295; 525/296; 527/312
[58] Field of Search .............. 525/252, 256, 261, 281

[56] References Cited

U.S. PATENT DOCUMENTS

| | | | |
|---|---|---|---|
| 3,050,390 | 8/1962 | Levinos et al. | 96/35 |
| 3,478,001 | 11/1969 | Szita et al. | 260/79.3 |
| 4,251,651 | 2/1981 | Kawakami et al. | 526/204 |
| 4,440,228 | 4/1984 | Swanson | 166/274 |
| 4,460,732 | 7/1984 | Buscall et al. | 524/460 |
| 4,471,097 | 9/1984 | Uhl et al. | 526/240 |
| 5,075,399 | 12/1991 | Ahmed et al. | 526/287 |
| 5,098,970 | 3/1992 | Hsieh et al. | 526/287 |
| 5,106,929 | 4/1992 | Ahmed et al. | 526/240 |
| 5,130,389 | 7/1992 | Ahmed et al. | 526/240 |
| 5,130,391 | 7/1992 | Ahmed et ai. | 526/288 |

OTHER PUBLICATIONS

Polymer, vol. 19, pp. 1157-1162 (Salamone et al, Oct. 1978).
J. Appl. Poly. Sci., vol. 22, pp. 1343-1357 (1978).
Encyclopedia of Polymer Science and Engineering, vol. 11, pp. 514-530 (1988).

*Primary Examiner*—Joseph L. Schofer
*Assistant Examiner*—Wu C. Cheng
*Attorney, Agent, or Firm*—Lucas K. Shay

[57] ABSTRACT

Polymer compositions which are highly absorbent to aqueous electrolyte solutions are prepared by copolymerization of an ampholytic monomer having the formula of

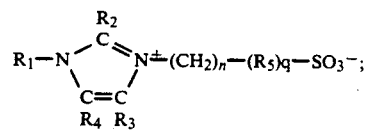

where one and only one of the substituted groups $R_1$, $R_2$, $R_3$ and $R_4$ must be a vinyl group, the rest can be the same or different and can be hydrogen or a $C_1$–$C_3$ alkyl group; $R_5$ is a phenyl group; n is $\geq 1$ and $\leq 6$; and q is 0 or 1; and an olefin monomer having an ethylenic structure as well as by graft copolymerization of at least an olefin monomer having an ethylenic structure and an ampholytic monomer having the formula disclosed above onto a main polymer selected from the group consisting of polysacchardies and polyolefins. Also disclosed is a process for absorbing large quantity of aqueous electrolyte solution employing the polymer compositions.

16 Claims, No Drawings

SUPERABSORBENT POLYMERS

This application is a divisional of application Ser. No. 07/873,259, filed Apr. 24, 1992, now U.S. Pat. No. 5,225,506.

FIELD OF THE INVENTION

The present invention relates to polymers capable of absorbing aqueous electrolyte solutions.

BACKGROUND OF THE INVENTION

Polymers for absorbing aqueous electrolyte solutions are used in numerous commercial and industrial applications. For example, polymers are used to improve the water absorbency of paper towels and disposable diapers.

Though known water absorbing polymers are highly absorbent to deionized water, they are dramatically less absorbent to aqueous electrolyte solutions such as salt water, brine, and urine. For example, hydrolyzed crosslinked polyacrylamide absorbs 1,024 grams of deionized water per gram of polymer, but only 25 grams of synthetic urine per gram of polymer. Crosslinked polyacrylate absorbs 423 grams of deionized water per gram of polymer, but only 10 grams of synthetic urine per gram of polymer. Hydrolyzed crosslinked polyacrylonitrile absorbs 352 grams of deionized water per gram of polymer, but only 25 grams of synthetic urine per gram of polymer. Analogous starch grafted copolymers generally have very poor absorbency to synthetic urine.

It would be a valuable contribution to the art to develop polymers with high absorbency to aqueous electrolyte solutions. It also would be a valuable contribution to the art to develop biodegradable graft copolymers which were highly absorbent to aqueous electrolyte solutions. The market for these types of copolymers is large and the uses are numerous. Therefore, seemingly small improvements in the absorbency translate into large savings in the quantity of copolymer required to absorb these liquids and large savings to the consumer.

SUMMARY OF THE INVENTION

Thus, it is an object of the present invention to provide polymers which are highly absorbent to aqueous electrolyte solutions. It is also an object of the present invention to provide a process for preparing the polymers having high absorbency to aqueous electrolyte solutions. Another object of the present invention is to provide biodegradable polymers which are highly absorbent to aqueous electrolyte solutions. A further object of the present invention is to provide a method of using the polymers of the present invention for absorbing an aqueous electrolyte solution.

Further objects, features, and advantages of the present invention will be readily apparent to those skilled in the art upon reading the description of the invention which follows.

According to a first embodiment of the present invention, a polymer having a high absorbency to aqueous electrolyte solutions is provided which comprises repeating units derived from: (a) an ampholytic monomer having the formula of:

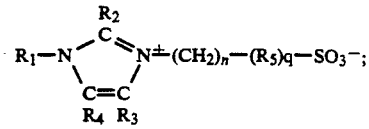

where one and only one of the substituted groups $R_1$, $R_2$, $R_3$ and $R_4$ must be a vinyl group, the rest can be the same or different and is a hydrogen or a $C_1$–$C_3$ alkyl group; $R_5$ is a phenyl group; n is $\geq 1$ and $\leq 6$; and q is 0 or 1; (b) at least one comonomer selected from the group consisting of acrylamide, methacrylamide, acrylonitrile, acrylic acid, methacrylic acid, alkali salts of acrylic acid, alkali salts of methacrylic acid, 2-methacryloyloxyethyltrimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 3-methacrylamidopropyltrimethylamine, 3-methacrylamidopropyldimethylamine, 2-methacryloyloxyethyldiethylamine, styrene sulfonic acid, alkali salts of styrene sulfonic acid, and N-vinyl-2-pyrrolidone; and (c) at least one crosslinking agent which has at least two polymerizable olefinic functionalities wherein the olefinic functionalities are suitable for crosslinking.

According to a second embodiment of the present invention, a graft copolymer having a high absorbency to aqueous electrolyte solutions is prepared by contacting a main polymer chain selected from the group consisting of a polysaccharides and a polyolefins under graft polymerization conditions with (a) at least one olefin monomer selected from the group consisting of acrylamide, methacrylamide, acrylonitrile, acrylic acid, methacrylic acid, alkali salts of acrylic acid, alkali salts of methacrylic acid, 2-methacryloyloxyethyldiethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 3-methacrylamidopropyltrimethylamine, 3-methacrylamidopropyldimethylamine, 2-methacryloyloxyethyldiethylamine, styrene sulfonic acid, alkali salts of styrene sulfonic acid, and N-vinyl-2-pyrrolidone; and (b) an ampholytic monomer having the formula of:

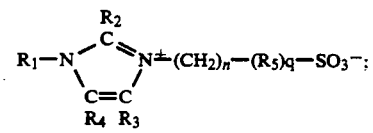

where one and only one of the substituted groups $R_1$, $R_2$, $R_3$ and $R_4$ must be a vinyl group, the rest can be the same or different and can be hydrogen or a $C_1$–$C_3$ alkyl group; $R_5$ is a phenyl group; n is $\geq 1$ and $\leq 6$; and q is 0 or 1.

According to a third embodiment of the present invention, a process for absorbing an aqueous electrolyte solution comprises contacting superabsorbent polymer selected from the group consisting of a graft copolymer which is prepared by contacting a main polymer chain selected from the group consisting of polysaccharides and polyolefins under graft polymerization conditions with (a) at least one olefin monomer selected from the group consisting of acrylamide, methacrylamide, acrylonitrile, acrylic acid, methacrylic acid, alkali salts of acrylic acid, alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 2-methacryloyloxyethyldiethylamine, 3-methacrylamidopropyldimethylamine, styrene sulfonic acid, alkali salts of styrene sulfonic acid, and N-vinyl-2-pyrrolidone; and (b) copolymerizing therewith an ampholytic monomer having the formula of:

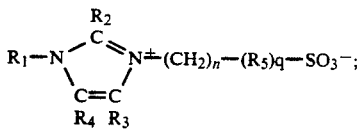

where one and only one of the substituted groups $R_1$, $R_2$, $R_3$ and $R_4$ must be a vinyl group, the rest can be the same or different and can be hydrogen or a $C_1$–$C_3$ alkyl group; $R_5$ is a phenyl group; n is $\geq 1$ and $\leq 6$; and q is 0 or 1; and an absorbent polymer which is prepared by copolymerization of (a) an ampholytic monomer having the formula of:

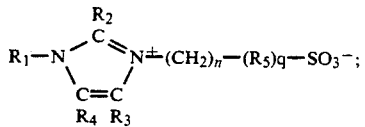

where one and only of the substituted groups $R_1$, $R_2$, $R_3$ and $R_4$ must be a vinyl group, the rest can be the same or different and can be hydrogen or a $C_1$–$C_3$ alkyl group; $R_5$ is a phenyl group; n is $\geq 1$ and $\leq 6$; and q is 0 or 1; (b) at least one comonomer selected from the group consisting of acrylamide, methacrylamide, acrylonitrile, acrylic acid, ethacrylic acid, alkali salts of acrylic acid, alkali salts of methacrylic acid, 2-methacryloyloxyethyltrimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 2-methacryloyloxyethyldiethylamine, 3-methacrylamidopropyldimethylamine, styrene sulfonic acid, alkali salts of styrene sulfonic acid, and N-vinyl-2-pyrrolidone; and (c) at least one crosslinking agent which has at least two polymerizable olefinic functionalities wherein the olefinic functionalities are suitable for crosslinking; with an aqueous electrolyte solution.

DETAILED DESCRIPTION OF THE INVENTION

The present invention provides a polymer that is highly absorbent to aqueous electrolyte solutions. Typical aqueous electrolyte solutions include, but are not limited to the group consisting of tap water, salt water, brine and urine. The term "polymer" used here generically refers to a polymer having two or more different monomers, i.e. copolymers, terpolymers, tetrapolymers, etc., and includes those prepared by copolymerization of an effective amount of each of the following monomers to produce a polymer that has the above-described properties: (a) an ampholytic monomer having the formula of:

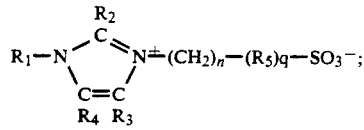

where at least and only one of the substituted groups $R_1$, $R_2$, $R_3$ and $R_4$ must be a vinyl group, the rest can be the same or different and can be hydrogen or a $C_1$–$C_3$ alkyl group; $R_5$ is a phenyl group; n is $\geq 1$ and $\geq 6$; and q is 0 or 1; (b) at least one comonomer selected from the group consisting of acrylamide, methacrylamide, acrylonitrile, acrylic acid, methacrylic acid, alkali salts of acrylic acid, alkali salts of methacrylic acid, 2-methacryloyloxyethyltrimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 2-methacryloyloxyethyldiethylamine, 3-methacrylamidopropyldimethylamine, styrene sulfonic acid, alkali salts of styrene sulfonic acid, and N-vinyl-2-pyrrolidone; and (c) at least one crosslinking agent which has at least two polymerizable olefinic functionalities wherein the olefinic functionalities are suitable for crosslinking.

Unless otherwise indicated, the term "alkali salts" is generically used in this application to mean salts containing ammonium cation and alkali metal cations such as lithium, sodium and potassium.

The presently preferred ampholytic monomer of the present invention is a hydroxide form in aqueous solution and is selected from the group consisting of 1-vinyl-3-(3-sulfopropyl)-imidazolium hydroxide, 1-vinyl-3-(4-sulfobutyl)imidazolium hydroxide, 1-vinyl-2-methyl-3-(3-sulfopropyl)imidazolium hydroxide, 1-vinyl-2-methyl-3-(4-sulfobutyl)imidazolium hyroxide, 1-vinyl-3-(2-sulfobenzyl)imidazolium hydroxide, 2-vinyl-3-(3-sulfopropyl)imidazolium hydroxide, 2-vinyl-3-(4-sulfobutyl)imidazolium hydroxide, 4(5)-vinyl-1-(3-sulfopropyl sulfobutyl)imidazolium hydroxide, 4(5)-vinyl-1-(4-sulfobutyl)imidazolium hydroxide, 1-methyl-2-vinyl-3-(3-sulfopropyl)imidazolium hydroxide and 1-vinyl-3-(4-sulfobutyl)imidazolium hydroxide. The presently preferred ampholytic monomer is 1-vinyl-3-(3-sulfopropyl)-imidazolium hydroxide (hereinafter referred to as VSPIH).

The olefinic comonomers can include, but are not limited to the group consisting of acrylamide, methacrylamide, acrylonitrile, acrylic acid, methacrylic acid, alkali salts of acrylic acid, alkali salts of methacrylic acid, 2-methacryloyloxyethyltrimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 2-methacryloyloxyethyldiethylamine, 3-methacrylamidopropyldimethylamine, styrene sulfonic acid, alkali salts of styrene sulfonic acid, N-vinyl-2-pyrrolidone and combinations of two or more thereof. These comonomers are believed to be commercially available.

Suitable crosslinking agents can include but are not limited to the group consisting of N,N-diallylmethacrylamide, diallylamine, N,N-bisacrylamidoacetic acid, N,N'-bisacrylamidoacetic acid methylester, N,N'- methylenebisacrylamide (methylene-bis-acrylamide), N,N-benzylidenebisacrylamide, allylacrylate, diisopropenylbenzene, diallyl succinate, ethylene glycol diacrylate, diallylacrylamide, divinylbenzene, and combinations of two or more thereof. All these suitable crosslinking agents are commercially available. The presently preferred crosslinking agent is N,N'-methylenebisacrylamide.

The polymers of the present invention are generally prepared by mixing the various monomers in desired stoichiometric ratios in aqueous solution and then initiating the free-radical copolymerization. The copolymerization of a ampholytic monomer with an olefinic comonomer and a crosslinking agent can be achieved by any of the well known free-radical polymerization techniques in solution, suspension, or emulsion environment. Well known azo compounds commonly employed to initiate free radical polymerization reactions include 2,2'-azobis(N,N'-dimethylisobutyramidine) dihydrochloride, azobisisobutyronitrile, 4,4'-azobis(4-cyanovaleric acid), 2,2'-azobis(2,4-dimethyl(4-methoxyvaleronitrile), 2,2'-azobis(2,4-dimethylvaleronitrile), 2,2'-azobis(2-amidinopropane)-dihydrochloride, 2-t-butylazo-2-cyano-4-methoxy-4-methylpentane, and 2-t-butylazo-2-cyano-4-methylpentane, and 4-t-butylazo-4-cyanovaleric acid. Well known inorganic peroxide compounds commonly employed to initiate free radical polymerization reactions include hydrogen peroxide, alkali metal persulfates, alkali metal perborates, alkali metal perphosphates, and alkali metal percarbonates. Well known organic peroxide compounds commonly employed to initiate free radical polymerization reactions include lauryl peroxide, 2,5-dimethyl-2,5-bis(2-ethylhexanoylperoxy)hexane, t-butylperoxyprivilate, t-butylperoctoate, p-methane hydroperoxide, and benzoylproxide. The compound t-butylhyponitrite is a well known alkyl hyponitrite commonly employed to initiate free radical polymerization reactions. Furthermore, ultraviolet light is commonly employed to initiate free radical polymerization reactions. In addition, such other methods of copolymerization as would have occurred to one skilled in the art may be employed, and the present invention is not limited to the particular method of preparing the polymer set out herein.

These inventive copolymers of the present invention containing an olefinic comonomer with amine, amide, nitrile, carboxylic acid, or sulfonic acid functionalities or crosslinking agent with amide, nitrile, carboxylic acid, or sulfonic acid functionalities can optionally be at least partially hyrolyzed and/or neutralized by heating with aqueous base such as aqueous sodium hydroxide or aqueous potassium hydroxide. The degree of hydrolysis and/or neutralization can be controlled by stoichiometrically limiting the amount of base relative to the amount of amide, nitrile, carboxylic acid, and sulfonic acid functionalities. If the hydrolysis is carried out under acidic conditions, the amide and nitrile functionalities can be converted to carboxylic acid functionalities without neutralizing the carboxylic acid or sulfonic acid functionalities of the polymer.

The polymers of the present invention can also optionally be saponified. The term "saponified" used herein, unless otherwise indicated, is the same as at least partially hydrolyzed and/or neutralized of the nitrile or amide functionalities by heating the polymer with an aqueous base. The presently preferred base is selected from the group consisting of lighium hydroxide, sodium hydroxide, potassium hydroxide, ammonium hydroxide, calcium hydroxide, and mixtures thereof. The presently preferred base is sodium hydroxide. Hydrolysis of these functionalities can be carried out under acidic or basic conditions. Under basic conditions, it generally also includes neutralization of carboxylic acid and sulfonic acid functionalities. The degree of hydrolysis and/or neutralization can be controlled by stoichiometrically limiting the amount of base relative to the amount of amide, nitrile, carboxylic acid, and sulfonic acid functionalities.

The mole percent of the ampholytic monomer of the present invention ranges from about 1 to about 60, preferably from about 2 to about 50, and most preferably 3 to 30. The mole percent of the comonomers(s) ranges from about 40 to about 99, preferably from about 50 to about 98, and most preferably from 70 to 97. The total mole percent of the ampholytic monomer and the comonomer equals to 100 mole percent. The crosslinking agent is provided in an amount effective to produce a highly absorbent copolymer. The mole percent of the crosslinking agent can be from about 0.001 to about 5, preferably from about 0.01 to about 2.5, and most preferably from 0.02 to 1 based on the total mole percent of the polymer.

The second embodiment of the present invention provides grafted polymers that are highly absorbent to aqueous electrolyte solutions. Grafted polymers as used herein are polymers of one or more species of monomers connected to a main chain as a side chain, exclusive of branch point on the main chain. Side chains of a grafted polymer are distinguished from the main polymer chain by the monomer constitution of the side chain i.e., the side chains comprise units derived from at least one species of monomer different from those that supply the units of the main polymer chain. The main polymer chain as utilized in the present invention are homopolymeric and copolymeric polymer such as polysaccharides, polypropylene, polyethylene and other polyolefins. The side chains are formed of at least one olefinic comonomer and an ampholytic monomer.

The term "graft copolymerization" is used herein, unless otherwise indicated, to mean a copolymer which results from the formation of an active site or sites at one or more points on the main chain of a polymer molecule other than its end and exposure to at least one other monomer. The graft polymers of the present invention are prepared by graft copolymerization of an effective amount of each of the following components onto a first polymer (main polymer chain) to produce a highly absorbent polymer: at least one comonomer selected from the group consisting of acrylamide, methacrylamide, acrylonitrile, acrylic acid, methacrylic acid, alkali salts of acrylic acid, alkali salts of methacrylic acid, 2-methacryloyloxyethyldiethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 2-methacryloyloxyethyldiethylamine, 3-methacrylamidopropyldimethylamine, styrene sulfonic acid, alkali salts of styrene sulfonic acid, and N-vinyl-2-pyrrolidone to form a first grafted polymer; and thereafter graft copolymerizing therewith an ampholytic monomer having the formula of:

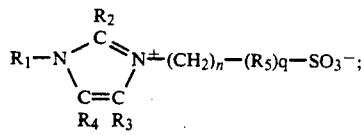

where one and only one of the substituted groups $R_1$, $R_2$, $R_3$ and $R_4$ must be a vinyl group, the rest can be the same or different and can be hydrogen or a $C_1$–$C_3$ alkyl group; $R_5$ is a phenyl group; n is $\geq 1$ and $\leq 6$; and q is 0 or 1.

It should be noted, however, the ampholytic monomer can also be graft copolymerized onto the first polymer to form a first grafted copolymer and thereafter graft copolymerized therewith at least one comonomer selected from the group described above.

Polymers which may be used as main chains in the practice of the present invention include polysaccharides and polyolefins. Polysaccharides suitable for the practice of the present invention include starches, celluloses and glycogens. Common sources of cellulose include but are not limited to cotton, linen, rayon, wood pulp and cellulose xanthine. Currently, cotton gauze is preferred. Suitable starches included swollen amylose and amylopectin starches. For the practice of the present invention, these starches should be swollen by heating the starch in water to substantially dissolve the starch granules. Preferably starches used in the present invention will have less than 30 weight percent amylose based on the weight of the dry starch before graft copolymerization. The preferred starch for use in grafting is soluble starch flour within the range of from about 0 to about 20 weight percent amylose content. Suitable polyolefins include polypropylene and polyethylene. The polypropylene suitable for use as main polymer chain includes polypropylene homopolymers, polypropylene copolymer and polypropylene block-copolymers. The polyethylene suitable for use as a main polymer chain includes polyethylene homopolymer, polyethylene copolymers and polyethylene block-copolymers. Preferably the synthetic polymers listed above will be utilized in the form of filaments or thin sheets so that a high surface area to mass will be provided for grafting therewith the comonomers and ampholytic monomer. Filaments utilized for grafting will preferably have a denier ranging from about 1 to about 20 denier and most preferably in the range of about 1 to 8 denier.

The term "monomer" is used generically, unless otherwise indicated, to mean monomers, comonomers, termonomers, tetramonomers, etc. The term "comonomer" is used generically, unless otherwise indicated, to mean monomers, comonomers, termonomers, tetramonomers, etc. for polymers wherein there are at least two different monomer.

The scope of the olefinic comonomer and the ampholytic monomer are the same as those described above.

The polymers of the second embodiment of the present invention are generally prepared in a two step process, though a single graft copolymerizing step or more than two grafting and polymerizing steps may be advantageously employed. The purpose of the two step process is to provide a first grafted polymer wherein the grafted comonomer side chains are more reactive to the polymerization of the ampholytic monomer. Some systems may be reactive enough so that a two step process is not necessary to provide grafted copolymers which are highly absorbent to aqueous electrolyte solutions. Alternatively, the multiple step process may be advantageously employed to control the proportions of monomers and relative lengths of the block copolymer chains by graft copolymerizing the various monomers in the desired stochiometric ratios at the appropriate step of the process.

In the preparation of polysaccharide grafted polymers, it is preferred that as a first step, at least one of the comonomers is graft copolymerized onto a polysaccharide, to produce a first polysaccharide graft copolymer. Then in a second step, the ampholytic monomer is graft copolymerized onto the polysaccharide or the ampholytic monomer is polymerized onto the grafted comonomer side chains. At the second or any subsequent graft copolymerizing step, the ampholytic monomer may be copolymerized with at least one other comonomer. At the second step or any subsequent graft copolymerizing step, the ampholytic monomer may be copolymerized with at least one comonomer which has a polymerizable olefinic functionality selected from the group consisting of acrylamide, methacrylamide, acrylonitrile, acrylic acid, methacrylic acid, alkali salts of acrylic acid, alkali salts of methacrylic acid, 2-methacryloyloxyethyldiethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid and N-vinyl-2-pyrrolidone.

The graft copolymerization of the ampolytic monomer may require a higher temperature than the graft polymerization of some of the other comonomers. Therefore, for the graft copolymerization at temperatures in the range of from about 0° C. to about 90° C. and preferably in the range of from about 40° C. to about 70° C. Those skilled in the art will recognize that the temperatures at which the polymerization is carried out should be varied to allow the various monomers and comonomer to react completely within a reasonable period of time for the method of polymerization utilized.

Most graft copolymerization methods for olefinic monomers involve the creation of reactive sites (for example free-radicals) on the main polymer chain. These reactive sites then serve to initiate the copolymerization of the other monomers onto the main copolymer chain. Free-radicals reactive sites on the main chain generally are produced by high energy radiation or chemical initiation. A common chemical means for creating these free-radicals within polysaccharide polymers and polypropylene polymers is with a chemical oxidation-reduction system. Examples of such oxidation-reduction systems include but are not limited to oxidation-reduction systems selected from the group consisting of ceric ammonium nitrate/nitric acid, ceric ammonium sulfate/sulfuric acid, potassium permanganate/oxalic acid, hydrogen peroxide/ferrous alkali salts, hydrogen peroxide/ascorbic acid and amine/persulfate. Common irradiation means for producing free radicals on the main polymer chain is by utilizing a gamma radiation source (i.e. cobalt to) or an electron beam.

The copolymerization of the ampholytic monomer with the olefinic comonomer onto the grafted comonomer side chains can be achieved by any of the well known free-radical polymerization techniques in solution, suspension, or emulsion environment. The techniques are the same as those described above.

Optionally, the inventive graft polymers of the present invention can be crosslinked with a suitable crosslinking agent. The crosslinking agents and the crosslinking techniques are the same as those described above.

The relative amount of the main polymer chain to the total weight of the comonomer and ampholytic monomer can be chosen to provide a grafted polymer of variable absorbency. However, the main polymer chain generally constitutes in the range of from about 1 to about 50 weight percent, and preferably from 5 to 30 weight percent of the total weight of comonomers, ampholytic monomer and main polymer chain present. The mole percent of comonomer and ampholytic monomer which may be graft copolymerized onto the main polymer chain is in the range of from about 75 to about 98 and from about 2 to about 25, respectively; and preferably from 80 to 97 and from 3 to 20, respectively, based on the total moles of the comonomers and ampholytic ion pair totaling a 100 percent.

According to the third embodiment of the present invention, a process for absorbing aqueous electrolyte solutions comprises contacting an absorbent polymer selected from the group consisting of a polymer prepared by copolymerizing: (a) an ampholytic monomer having the formula of:

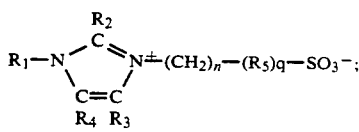

where one and only one of the substituted groups $R_1$, $R_2$, $R_3$ and $R_4$ must be a vinyl group, the rest can be the same or different and can be hydrogen or a $C_1$-$C_3$ alkyl group; $R_5$ is a phenyl group; n is $\geq 1$ and $\leq 6$; and q is 0 or 1; (b) at least one comonomer selected from the group consisting of acrylamide, methacrylamide, acrylonitrile, acrylic acid, ethacrylic acid, alkali salts of acrylic acid, alkali salts of methacrylic acid, 2-methacryloyloxyethyltrimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 2-methacryloyloxyethyldiethylamine, 3-methacrylamidopropyldimethylamine, styrene sulfonic acid, alkali salts of styrene sulfonic acid, and N-vinyl-2-pyrrolidone; and (c) at least one crosslinking agent which has at least two polymerizable olefinic functionalities wherein the olefin functionalities are suitable for crosslinking; and a graft polymer prepared by contacting a first polymer selected from the group consisting of polysaccharides, polyolefins with: (a) at least one olefin monomer selected from the group consisting of acrylamide, methacrylamide, acrylonitrile, acrylic acid, methacrylic acid, alkali salts of acrylic acid, alkali salts of methacrylic acid, 2-methacryloyloxyethyldiethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 2-methacryloyloxyettyldiethylamine, 3-methacrylamidopropyldimethylamine, styrene sulfonic acid, alkali salts of styrene sulfonic acid, and N-vinyl-2-pyrrolidone; and (b) copolymerizing therewith an ampholytic monomer having the formula of:

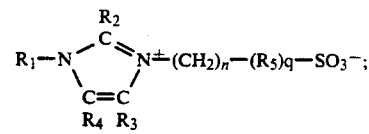

where one and only one of the substituted groups $R_1$, $R_2$, $R_3$ and $R_4$ must be a vinyl group, the rest can be the same or different and can be hydrogen or a $C_1$-$C_3$ alkyl group; $R_5$ is a phenyl group; n is $\geq 1$ and $\leq 6$; and q is 0 or 1.

Typical aqueous electrolyte solutions include but are not limited to electrolyte solutions selected from the group consisting of tap water, salt water, brine, and urine. For the purpose of this invention, tap water is defined to have an electrolyte concentration of less than 500 ppm of dissolved electrolytes, urine is defined to have an electrolyte concentration of from greater than 500 ppm to at most 10,000 ppm of dissolved electrolytes, salt water is defined to have an electrolyte concentration from greater than 10,000 ppm to at most 34,000 ppm and brine is defined to have an electrolyte concentration of from greater than 34,000 ppm to the saturation point of the solution.

The scope of the absorbent polymer and grafted polymer is the same as that described above.

The following examples are provided to illustrate the advantages of the present invention and are not intended to unduly limit the present invention.

COMPARATIVE EXAMPLE I

This comparative example shows the absorbency of known crosslinked polymers.

The crosslinked polymers were prepared by mixing the monomers in the proportions given in Table I in an aqueous solution of deionized water. The monomers were present in 30–40 weight % relative to the amount of deionized water. The free radical polymerization was initiated with commercially available 2,2'-azobis(N,N'-dimethylisobutyramidine) dihydrochloride. The reaction mixture was then degassed by bubbling nitrogen gas through the mixture for 15 minutes. The amount of the azo free-radical initiator employed was 0.1 mole percent, based on the total moles of the monomers. The reaction temperature was maintained between 20°–35° C. for 24 hours. The reactions produced transparent or cloudy hard gels of the crosslinked polymers. A large volume (1,000 ml for 6 gram gel) of deionized water was added to the polymer product and the polymers were allowed to swell for about 24 hours. The swelled polymers were dried in a forced air convection oven at 74° F. The dried polymers were then mechanically blended into a powder.

Some of the crosslinked polymers were hydrolyzed or neutralized with a strong base such as aqueous sodium hydroxide or aqueous potassium hydroxide. The degree of hydrolysis or neutralization was controlled by stoichiometrically limiting the amount of base relative to the amount of amide, nitrile, or carboxylic acid functionalities. For these examples, a stoichiometric excess of the amount of base was used. A suspension of 1 gram of the polymer in about 20 ml of 0.5N aqueous sodium hydroxide was heated to 95° C. until a light golden-yellow color was obtained. The mixture was then transferred to a dialysis bag with a molecular weight cut-off of 12,000–14,000 and dialyzed exhaustively against distilled water until the viscous polymer gel had reached pH 7. This viscous polymer gel was then poured into a plastic dish and dried in a forced air convection oven at 74° C. The dried polymers were then mechanically blended to a powder.

The crosslinked polymers were then tested for deionized water absorption and synthetic urine absorption. About 1 liter of deionized water or synthetic urine was added to 0.1 to 0.5 gram of the dried polymer and allowed to stand for 24 hours. The polymer was then separated from the excess unabsorbed liquid by screening through a 100 mesh per inch stainless steel sieve. The absorbency was determined by weighing the isolated polymer containing the absorbed liquid and subtracting the weight of the dry polymer.

The absorbency was measured in units of grams of liquid per grams of polymer. The synthetic urine was prepared by dissolving 0.64 gram $CaCl_2$, 1.14 gram $MgSO_4 \cdot 7H_2O$, 8.20 gram NaCl, and 20.0 gram urea into 1000 gram deionized water. Several of the polymers were tested two or three times, and the experimental error was within plus or minus 2–5 percent. This small experimental error was largely caused by gel blocking and minor diffusion problems that prevented the aqueous liquid from contacting with all the polymer. The results are shown in Table I.

strate, which comprises a large portion of the material, is very poorly absorbent to aqueous liquids of all kinds. This control data can be used to show that the polysaccharide grafted VSPIH copolymers of the present invention can effectively compete with these known crosslinked polymers and exceed the absorbency of these known crosslinked polymers. Furthermore, these known crosslinked polymers have questionable biodegradeability.

Known polymer compositions include crosslinked polyacrylamide, partially saponified crosslinked polyacrylamide, crosslinked polyacrylonitrile, partially saponified crosslinked acrylonitrile, crosslinked polyacrylic acid, neutralized crosslinked polyacrylic acid, crosslinked polyacrylate, and polymers thereof with sodium 2-acrylamido-2-methylpropane sulfonate. The best of these known polymers absorb up to 65 g of synthetic urine per g of polymer, and most of the known polymers absorb much less than 50 g of synthetic urine per of g of polymer.

COMPARATIVE EXAMPLE II

The data in Table II demonstrates that although commercially available water absorbing materials are highly absorbent to water, they are also dramatically less absorbent to aqueous electrolyte solutions such as salt water and urine. The commercially available water absorbing materials tested include poly(co-acrylamide-

TABLE I

Control Data for Known Crosslinked Polymers

| RUN # | AMPS ® | Mole Percent | | | | Mole Ratio* | XOH | g/g** | |
|---|---|---|---|---|---|---|---|---|---|
| | | AM | AN | AA | X-AA | LINK | | DIW | SU |
| 1 | — | 100 | — | — | — | 0.05 | NO | 17 | 15 |
| 2 | — | 100 | — | — | — | 0.05 | YES | 1024 | 25 |
| 3 | — | 100 | — | — | — | 0.05 | YES | 364 | 40 |
| 4 | — | 100 | — | — | — | 0.20 | NO | 13 | 12.5 |
| 5 | — | 100 | — | — | — | 0.20 | YES | 295 | 16 |
| 6 | — | — | 100 | — | — | 0.05 | YES | 608 | 46 |
| 7 | — | — | 100 | — | — | 0.10 | NO | 0 | 0 |
| 8 | — | — | 100 | — | — | 0.10 | YES | 414 | 42 |
| 9 | — | — | 100 | — | — | 0.20 | YES | 352 | 25 |
| 10 | — | — | — | 100 | — | 0.20 | NO | 21 | 11 |
| 11 | — | — | — | 100 | — | 0.20 | Neu+ | 423 | 10 |
| 12 | — | — | — | — | 100 (K) | 0.05 | NO | 669 | 57 |
| 13 | — | — | — | — | 100 (Na) | 0.05 | NO | 505 | 41 |
| 14 | — | 13 | — | — | 87 | 0.05 | NO | — | 65 |
| 15 | 3 | 13 | — | — | 84 | 0.05 | NO | 350 | 38 |
| 16 | 3 | 20 | — | — | 77 | 0.05 | NO | 417 | 47 |
| 17 | 6 | 13 | — | — | 81 | 0.05 | NO | 738 | 56 |
| 18 | 6 | 26 | — | — | 68 | 0.05 | NO | 533 | 47 |
| 19 | 6 | — | — | — | 94 | 0.05 | NO | 488 | 55 |
| 20 | 10 | 13 | — | — | 77 | 0.05 | NO | 570 | 59 |
| 21 | 20 | 13 | — | — | 67 | 0.05 | NO | 624 | 62 |
| 22 | 100 | — | — | — | — | 0.05 | NO | Soluble | |

AMPS ® = 2-acrylamido-2-methylpropane sulfonate (Note: AMPS ® is a trademark of Lubrizol for 2-acrylamido-2-methylpropane sulfonic acid).
AM = Acrylamide
AN = Acrylonitrile
AA = Acrylic Acid
X-AA = Sodium Acrylate or Potassium Acrylate
LINK = Methylene-bis-acrylamide Crosslinking Agent
XOH = Basic Hydrolysis and/or Neutralization with aqueous NaOH or KOH
DIW = Deionized Water
SU = Synthetic Urine
*mole ratio = mole of the crosslinking agent per 100 mole of the ampholytic monomer and the comonomer
**g/g = absorbency units of gram aqueous liquid per gram dried polymer
+Neu = Neutralized The data in Table I demonstrates that although known crosslinked polymers are highly absorbent to deionized water, they are dramatically less absorbent to aqueous electrolyte solutions such as salt water and urine. Polysaccharide grafted polymers, however, according to their inherent nature, are normally much less absorbent to aqueous liquids. The polysaccharide subco-acrylic acid) grafted onto starch, a commercial acrylamide polymer sold under the trademark "Water Grabber" ® ("Water Grabber" is a trademark of F. P. Products, Inc.), "LUVS" ® diaper absorbent ("LUVS" is a trademark of Procter & Gamble Co.), "Pampers" ® diaper absorbent ("Pampers" is a trademark of Procter & Gamble Co.), and Favor 960" ® (Stockhausen, Inc.). The best of these known materials absorb up to about 56 grams of urine per gram of absorbing material, and most of the known polymers absorb much less than 40 grams of urine per gram of absorbing material.

The commercially available materials were tested for absorbency to aqueous liquids according to the method employed in Example I.

TABLE II

Control Data for Commercial Materials

| EXP # | commercial Material | DIW g/g* | SU g/g* |
|---|---|---|---|
| 1 | Commercial Starch-g-Poly(AM-AA) | 345 | 37 |
| 2 | Water Grabber ® (AM Copolymer) | 440 | 34 |
| 3 | Luvs ® Diaper Absorbent | 191 | 16 |
| 4 | Pampers ® Diaper Absorbent | 171 | 12 |
| 5 | Favor 960 ® | 369 | 56 | g = graft
AM = Acrylamide
AA = Acrylic Acid
DIW = Deionized Water
SU = Synthetic Urine
*g/g = absorbency units of gram aqueous liquid per gram dried polymer

EXAMPLE III

The homopolymers of the ampholytic monomer comprising VSPIH with 2.4 and 0.05 mole percent methylene-bis-acrylamide crosslinking agent was tested for their absorbency to deionized water and synthetic urine according to the method employed in Example I. The absorbency of homopolymers is very poor. See Table III. The absorbency to deionized water is about 0.77 gram to 3.00 grams water per grams of homopolymer, and only 1.07 and 4.00 grams of synthetic urine per gram of homopolymer, respectively.

TABLE III

Control Data for Homopolymer of Ampholytic Monomer

| | VSPIH | MBA* | Ag. Solvent Absorbency (g/g**) | |
|---|---|---|---|---|
| Run | Mole % | Mole Ratio | DIW | SU |
| 1 | 100 | 2.5 | 0.77 | 1.07 |
| 2 | 100 | 0.05 | 3.00 | 4.00 |

VSPIH = 1-vinyl-3-(3-sulfopropyl)imidazolium hydroxide
MBA = Methylene-bis-acrylamide
*Mole Ratio = mole of the crosslinking agent per 100 moles of the ampholytic monomer and comonomer
DIW = Deionized water
SU = Synthetic Urine
**g/g = Absorbency with 4 gram aqueous liquid per gram dried polymer

EXAMPLE IV

The polymers of this present invention were prepared according to the method described in Example I, except that the inventive polymers were prepared by mixing the monomers in the proportions given in Table IV. Some of these copolymers which contain amide and nitrile functionalities were hydrolyzed with an aqueous base such as sodium hydroxide or potassium hydroxide. This treatment resulted in slightly yellow coloration in the hydrolyzed products. All the copolymers were tested for absorbency in DIW and SU. The results given in Table IV demonstrate that these ampholytic copolymers exhibit significantly improved absorbency in the aqueous electrolyte solutions, such as SU, over the absorbency of the control polymer listed in Table I and the commercial polymers listed in Table II. Taking an absorbency of 35 g of SU per g of polymer for example (Run 1), it shows an improvement of about 118% over the SU absorbency of the equivalent control polymer Run 5 (Table I) or the "Luvs Diaper Absorbent" (Table II) which has apparently similar gel strength. Comparing an absorbency of 56 g of SU per g of the best commercial polymer, FAVOR 60 (Table II), the experimental polymer of apparently similar gel strength (Run 9) exceeds this absorbency in SU by about 71%.

TABLE IV[a]

Experimental Data for VSPIH Copolymers

| | Mole Percent | | | | | Mole Ratio* | | Absorbency (g/g) | |
|---|---|---|---|---|---|---|---|---|---|
| Run # | VSPIH | AM | AN | AA | X-AA | X-LINK | XOH | DIW | SU |
| 1 | 10 | 90 | — | — | — | 0.20 | Yes | 587 | 35 |
| 2 | 10 | 90 | — | — | — | 0.10 | Yes | 397 | 38 |
| 3 | 10 | 90 | — | — | — | 0.05 | Yes | 820 | 46 |
| 4 | 6 | 94 | — | — | — | 0.10 | Yes | 378 | 44 |
| 5 | 3 | 97 | — | — | — | 0.10 | Yes | 378 | 44 |
| 6 | 3 | 97 | — | — | — | 0.03 | Yes | 1400 | 55 |
| 7 | 10 | 90 | — | — | — | 0.03 | Yes | 1900 | 95 |
| 8 | 10 | 90 | — | — | — | 0.03 | Yes | 1900 | 95 |
| 9 | 15 | 85 | — | — | — | 0.03 | Yes | 1323 | 96 |
| 10 | 3 | — | 97 | — | — | 0.06 | Yes | — | 25 |
| 11 | 6 | — | 94 | 00 | 00 | 0.06 | Yes | — | 43 |
| 12 | 10 | — | 90 | — | — | 0.06 | Yes | — | 45 |
| 13 | 15 | — | 85 | — | — | 0.06 | Yes | — | 65 |
| 14 | 3 | 20 | — | — | 77 | 0.05 | No | 276 | 65 |
| 15 | 6 | 20 | — | — | 74 | 0.05 | No | 312 | 79 |
| 16 | 10 | 20 | — | — | 70 | 0.05 | No | 200 | 70 |

[a]See Table 1 footnotes for abbreviations.

EXAMPLE V

The polysaccharide grafted VSPIH copolymers of this present invention in Table V were generally prepared according to the following two step procedure.

About 5 grams of reagent grade soluble starch was added to 50 ml of deionized water. While stirring under inert nitrogen atmosphere, the soluble starch slurry was heated to 95° C. for 1 hr. after which the heat was removed and the stirred soluble starch slurry was allowed to cool to room temperature, about 22° C. A solution of 0.17 gram ceric ammonium nitrite in 1.5 ml of 1N nitric acid was added to the cooled stirring soluble starch slurry. After about 5 minutes, the olefinic comonomer (0.0659-0.0848 moles) was then added to the soluble starch slurry mixture. The particular comonomer and relative mole percent added for each of the tested polysaccharide grafted VSPIH copolymers is provided in Table V. The mixture was stirred under inert nitrogen atmosphere for two hours.

The mixture was then heated to 60° C., at which point a solution of 0.17 gram ceric ammonium nitrate in 1-5 ml of 1N nitric acid was added to the mixture. After about 1 minute, a 70 wt % solution of the ampholytic monomer dissolved in deionized water was added to the warmed mixture. The particulate VSPIH monomer and relative mole percent added for each of the tested polysaccharide grafted VSPIH copolymers is provided in Table V. This new mixture was stirred under nitrogen at 60° C. for another 6-8 hours.

The pH of the mixture was adjusted to between pH 4 and pH 5. The solid crude polysaccharide grafted VSPIH copolymers was obtained by evaporating the aqueous solvent in a forced air convection oven maintained at 74° C. The crude grafted polymer was washed by boiling in dimethylformamide to remove any non-grafted acrylonitrile homopolymer. It was then thoroughly washed with water to remove any water soluble polymer. The purified grafted material was finally washed with ethanol and dried in a vacuum oven at 70° C. for 24 hours. The dried polymers were then mechanically blended to a powder form. The yield of polysaccharide grafted VSPIH copolymers was typically in excess of 55 wt % based on the total weight of the soluble starch, comonomer, and ampholytic monomer.

Some of the inventive polysaccharide grafted VSPIH copolymers containing an olefinic comonomer with amine, amide, nitrile, carboxylic acid or sulfonic acid functionalities were hydrolyzed and/or neutralized with an aqueous base such as aqueous sodium or potassium hydroxide according to the method described in Example I. The polymers were recovered by drying in a forced air convection oven at 74° C. The dried polymers were then mechanically blended to a powder form.

The polysaccharide grafted VSPIH copolymers were tested for their absorbency according to the method employed in Example I.

TABLE V$^a$

Comparative Data with Graft Copolymer

| Run # | VSPIH Mole % | AN Mole % | Yield Weight Percent | XOH | Aqueous Solvent Absorbency g/g DIW | SU |
|---|---|---|---|---|---|---|
| 1 | — | 100 | 50 | Yes | 783 | 36 |
| 2 | 12 | 88 | 55 | Yes | 900 | 77 |
| 3 | 19.7 | 80.3 | 55 | Yes | 712 | 73.5 |

$^a$See footnotes of Table I for abbreviations.

As can be seen in table V, the grafted copolymers have much higher synthetic urine absorbency (77 and 73.5 g/g, runs 2 and 3, respectively) than control (Run 1 of Table V and Runs 1-2 of Table III).

Thus, the present invention is well adapted to carry out the objects and obtain the ends and advantages mentioned above as well as those inherent therein.

While presently preferred embodiments have been described for purposes of this disclosure, numerous changes will be apparent to those skilled in the art. Such changes are encompassed within the spirit of the invention as defined by the appended claims.

That which is claimed is:

1. A graft copolymer prepared by contacting a main polymer selected from the group consisting of polysaccharides, polyolefins, and mixtures thereof; under graft polymerization conditions with:

(a) at least one olefinic monomer having functionality selected from the group consisting of amine, amide, nitrile, carboxylic acid, sulfonic acid, and mixtures thereof; and (b) an ampholytic monomer having the formula of:

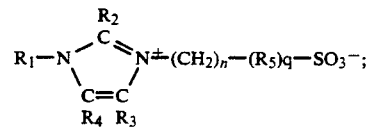

where one and only one of the substituted groups $R_1$, $R_2$, $R_3$ and $R_4$ must be a vinyl group, the rest can be the same or different and can be hydrogen or a $C_1$-$C_3$ alkyl group; $R_5$ is a phenyl group; n is $\geq 1$ and $\leq 6$; and q is 0 or 1.

2. A graft copolymer according to claim 1 wherein said olefinic monomer is first graft polymerized onto said main polymer to produce an olefin grafted main polymer chain and thereafter said ampholytic monomer is graft polymerized onto said olefin grafted main polymer chain.

3. A graft copolymer according to claim 1 wherein said ampholytic monomer is first graft copolymerized onto said main polymer to produce an ampholytic monomer grafted main polymer chain and thereafter said olefin monomer is graft copolymerized onto said ampholytic monomer grafted main polymer chain.

4. A graft copolymer according to claim 1 wherein a mixture of said olefinic monomer and said ampholytic monomer is graft polymerized onto said main polymer chain.

5. A graft copolymer according to claim 1 wherein said olefinic monomer is selected from the group consisting of acrylamide, methacrylamide, acrylonitrile, acrylic acid, methacrylic acid, alkali salts of acrylic acid, alkali salts of methacrylic acid, 2-methacryloyloxyethyldiethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, 3-methacrylamidopropyltrimethylamine, 3-methacrylamidopropyldimethylamine, 2-methacryloyloxyethyldiethylamine, styrene sulfonic acid, alkali salts of styrene sulfonic acid, N-vinyl-2-pyrrolidone, and mixtures thereof.

6. A graft copolymer according to claim 1 wherein contemporaneously with said graft polymerization a crosslinking agent is copolymerized therewith, wherein said crosslinking agent is provided in an amount effective to produce a highly absorbent graft copolymer.

7. A graft copolymer according to claim 6 wherein said crosslinking agent is N,N'-methylenebisacrylamide.

8. A graft copolymer according to claim 1 wherein said main polymer is a polysaccharide selected from the group consisting of starch, cellulose, glycogen, and mixtures thereof.

9. A graft copolymer according to claim 8 wherein said polysaccharide is starch.

10. A graft copolymer according to claim 1 wherein said ampholytic monomer is selected from the group consisting of 1-vinyl-3-(3-sulfopropyl)-imidazolium hydroxide, 1-vinyl-3-(4-sulfobutyl)imidazolium hydroxide, 1-vinyl-2-methyl-3-(3-sulfopropyl)imidazolium hydroxide, 1-vinyl-2-methyl-3-(4-sulfobutyl)imidazolium hydroxide, 1-vinyl-3-(2-sulfobenzyl)imidazolium hydroxide, 2-vinyl-3-(3-sulfopropyl)imidazolium hydroxide, 2-vinyl-3-(4-sulfobutyl)imidazolium hydroxide, 4(5)-vinyl-1-(3-sulfopropyl sulfobutyl)imidazolium hydroxide, 4(5)-vinyl-1-(4-sulfobutyl)imidazolium hydroxide, 1-methyl-2-vinyl-3-(3-sulfopropyl)imidazolium hydroxide, 1-vinyl-3-(4-sulfobutyl)imidazolium hydroxide, and mixtures thereof.

11. A graft copolymer according to claim 10 wherein said ampholytic monomer is 1-vinyl-3-(3-sulfopropyl)imidazolium hydroxide.

12. A graft copolymer according to claim 6 wherein said olefinic monomer is acrylonitrite.

13. A graft copolymer according to claim 1 wherein said grafted copolymer comprises: (a) from about 1 to about 50 weight % of said polysaccharide; and (b) from about 75 to about 98 mole % of said olefinic monomer and from about 2 to about 25 mole % of said ampholytic monomer based on total mole % of said olefinic monomer and ampholytic monomer equaling 100%.

14. A graft copolymer according to claim 13 wherein said grafted copolymer comprises: (a) from 5 to 30 weight % of said polysaccharide; and (b) from 80 to 97 mole % of said olefinic monomer and from 3 to 20 mole % of said ampholytic monomer based on total mole % of said olefinic monomer and said ampholytic monomer equaling 100%.

15. A graft copolymer according to claim 13 wherein said grafted copolymer comprises: (a) from 5 to 30 weight % of said starch; and (b) from 80 to 97 mole % of acrylonitrile and from 3 to 20 mole % of said 1-vinyl-3-(3-sulfopropyl)imidazolium hydroxide based on total mole % of acrylonitrile and 1-vinyl-3-(3-sulfopropyl)imidazolium hydroxide equaling 100%.

16. A graft copolymer according to claim 1 wherein said graft copolymer is partially hydrolyzed.

* * * * *